(12) United States Patent
Daniele et al.

(10) Patent No.: US 8,586,086 B2
(45) Date of Patent: Nov. 19, 2013

(54) HYDROGEL CAPABLE OF CONTAINING AND CONVEYING CELLS

(75) Inventors: Francesco Daniele, Milan (IT); Carmen Giordano, Naples (IT); Maurizio Masi, Milan (IT); Giuseppe Perale, Milan (IT); Filippo Rossi, Arezzo (IT); Marta Tunesi, Vanzago (IT)

(73) Assignee: Politecnico di Milano, Milan (IT)

( * ) Notice: Subject to any disclaimer, the term of this patent is extended or adjusted under 35 U.S.C. 154(b) by 162 days.

(21) Appl. No.: 12/994,873

(22) PCT Filed: May 29, 2009

(86) PCT No.: PCT/IB2009/005767
§ 371 (c)(1),
(2), (4) Date: Dec. 10, 2010

(87) PCT Pub. No.: WO2009/144569
PCT Pub. Date: Dec. 3, 2009

(65) Prior Publication Data
US 2011/0189285 A1   Aug. 4, 2011

(30) Foreign Application Priority Data

May 29, 2008   (IT) .............................. MI2008A1000
Nov. 17, 2008   (IT) .............................. MI2008A2037

(51) Int. Cl.
| | | |
|---|---|---|
| A61K 9/14 | (2006.01) |
| A61K 35/12 | (2006.01) |
| A61K 35/30 | (2006.01) |
| C12N 5/00 | (2006.01) |
| C12N 5/079 | (2010.01) |
| C12Q 1/02 | (2006.01) |
| A61P 9/00 | (2006.01) |
| A61P 19/04 | (2006.01) |
| A61P 27/02 | (2006.01) |
| A61P 17/00 | (2006.01) |
| A61P 1/16 | (2006.01) |
| A61P 13/12 | (2006.01) |
| A61P 25/00 | (2006.01) |
| A61P 25/28 | (2006.01) |
| A61P 25/16 | (2006.01) |

(52) U.S. Cl.
USPC ............. 424/484; 435/395; 435/29; 435/93.7

(58) Field of Classification Search
None
See application file for complete search history.

(56) References Cited

PUBLICATIONS

Lee et al. (Carbohydrate Polymers. 2000; 41(2): 197-205).*
Ramanan et al. (Biotechnol. Prog. 2006; 22: 118-125).*
Rossi et al. (Journal of Applied Polymer Science. 2012: 123: 2211-2221.*

* cited by examiner

*Primary Examiner* — Scott Long
(74) *Attorney, Agent, or Firm* — Jordan IP Law, LLC; Todd A. Vaughn

(57) ABSTRACT

An interpenetrating biodegradable polymeric matrix hydrogel and the use thereof to support, encapsulate, convey and release several types of cells under conditions which allow the cells to be kept alive, grow and interconnect. The hydrogel may be used to prepare implants for integrally or partially regenerating, reconstructing and/or replacing damaged, dead or no longer functional tissues, in particular at the central nervous system or spinal marrow level. In such use, the biodegradability of the hydrogel allows a progressive release of the conveyed cells in order to promote their integration, even functional, with the surrounding tissue. The hydrogel may also be employed to support cells, for example, neural cells such as neuronal cells, on measuring devices, specifically realized for monitoring several parameters of cell activity, also during pharmacological and bio-mechanical tests.

19 Claims, No Drawings

HYDROGEL CAPABLE OF CONTAINING AND CONVEYING CELLS

CROSS REFERENCE TO PRIOR APPLICATIONS

The present application is a National Stage Application of PCT International Application No. PCT/IB2009/005767 (filed on Nov. 29, 2009), under 35 U.S.C. 371, which claims priority to Italian Patent Application No. MI2008A001000 (filed on May 29, 2008) and Italian Patent Application No. MI2008A002037 (filed on Nov. 17, 2008), which are each hereby incorporated by reference in their respective entireties.

FIELD OF THE INVENTION

A double interpenetrating polymer matrix hydrogel formed by an acrylic acid-based or carbomeric polymer, a natural polymer, and a cross-linking agent. The hydrogel includes cells, for example, neuronal cells or central nervous system cells, placed on its external surface or housed within the tri-dimensional lattice formed by the polymeric matrix.

Object of the present invention is a double interpenetrating polymer matrix hydrogel formed by an acrylic acid-based or carbomeric polymer, a natural polymer, a cross-linking agent, said hydrogel containing cells, for example neuronal cells or central nervous system cells, placed on its external surface or housed within the tri-dimensional lattice formed by said polymeric matrix.

BACKGROUND OF THE INVENTION

When treating many pathologies, which lead to the degeneration of specific organs, the only possible therapeutic alternative is often represented by the organ transplantation. Where possible, however, it is associated to a high grade of risk for the patient, since complications are likely to occur, such as the transmission of pathologies from donor to recipient or the rejection of the organ itself, along with the chronic shortage of available organs. Moreover, such an approach cannot be applied to all the body zones susceptible to degenerative pathologies. Actually, at present, transplant therapies may not be applied to many degenerative pathologies, such as, in some cases, those related to some zones of the connective tissues, bone tissue, dermis and epidermis, besides the central nervous system and sometimes also the myocardium.

Since most cells of the central nervous system, for example neurons, do not proliferate nor renew, attention has been addressed to therapies based on replacement or regeneration of the damaged tissue, using isolated and re-grafted cells. In the recent history, the neural tissue engineering has mainly focused on Parkinson's disease [See, for example: Tabar et al., Nature Medicine (2008), doi:10,1038/nm1732] and on lesions in the spinal marrow [See, for example: Perale et al. Journal of Applied Biomaterials and Biomechanics (2008) vol. 6 pp. 1-8; Huang et al. Journal of Neurosurgery (2008) vol. 108 pp. 343-347; Nomura et al Journal of Neurotrauma (2006) vol. 23 pp. 496-507; Iwata et al. Tissue Engineering (2006) vol. 12 pp. 101-110], the relationships cause-effect involved in such diseases being well-known and effective therapies for treating the same being not available yet. In such a field, first experiments have been carried out, by directly transplanting or injecting aqueous suspensions of individual cells or cell populations.

The myocardial infarction pathologies represent a further well-known, representative case. Indeed, these are a common cause of death and lower quality of life all around the world. Following a heart attack, the myocardium suffers a more or less extended damage, which leads to lose the heart functionality and necrotic and non-functional tissues to be formed. When death is prevented, the chronic heart failure, at different levels, is a sure perspective. At the present state, for more serious stages of this pathology, effective pharmacological treatments are not available yet, and therefore, the transplantation is often the last, but unfortunately not always feasible, therapeutic opportunity. For less serious cases, the available treatments allow only to keep the clinical status quo. Therapies, which lead to significant improvement and recover for the myocardium, in fact, are not available [See, the monograph J. O. Mudd, D. A. Kass, Nature, volume 451: pp. 919-928, 2008]. The likelihood to inject specific healthy cells in the infarcted zones in order to cause the regeneration is arising as a possibly more successful way [as it is evident, for example, in the following monographs: M. N. Giraud et al., Tissue Eng 13(8): 1825-1836; 2008. V. F. M. Segers, R. T. Lee, Nature 451: 937-942; 2008. S. J. Dimmeler et al., Arterioscl. Thromb. Vasc. Biol. 28: 208-216, 2008].

The lower level of cell specialization in tissues with a strong connective component represents, perhaps, a better condition from several points of view, as some opportunities exist, to make bi- and tri-dimensional artificial structures capable of hosting and carrying specific cells for the functional recovery of damaged structures. These artificial devices, also known as scaffolds, represent one of the pillars of tissue engineering, but, of course, they are not free of problems [As an example, see the monograph C. H. Evans et al., Tissue Engineering, Volume 13(8), pp. 1987-1993, 2007]. In this field, a well known kind of damages is linked to those related to the cartilages, mostly the articular cartilages. The cartilaginous tissue is a particular kind of connective tissue, characterized by remarkable resistance and flexibility properties, which plays a role of structural support within the organism. It is a particular kind of connective tissue and, as such, it is composed of cells dispersed in much gelatinous extracellular matrix, rich in fibres (responsible for elasticity) and an amorphous substance originated from proteins. Articular cartilages are those, which cover the joint surfaces and those most known for being susceptible to traumas are those related to the knee. Of course, they are not lethal pathologies, but they are annoying and can lower the quality of life and be disabling. The surgical techniques developed aim to substantially reduce the defect, by eliminating the injured zone, but this exposes the joint to more friction and wear over the time. There are no substantially effective pharmacological treatments. Therefore, the regenerative medicine is deemed as the frontier for treating these pathologies, mostly those originating from traumas. Carrying chondrocytes and making them remain alive in situ is the basic setting for therapies under development, mainly based on two similar approaches: a) carrying the cells by using planar solid matrixes in the form of the defect to be integrated, b) carrying the cells through gels, which are injected until the defect to be integrated is filled. In both cases, the solutions tend to use biodegradable materials, in order to promote the integration [as shown, for instance, in the following monographs: Jorgensen C et al., Best Practice & Research In Clinical Rheumatology 22(2), pp. 269-284, 2008. Grayson W L et al., Trends In Biotechnology, (26)4, pp. 181-189, 2008].

Likewise, the degenerative pathologies regarding the bone tissues can result in a particularly severe structural fragility and the main therapies are pharmacological, which, however, do not always guarantee efficacy and are not devoid of side effects. However, also the tissue engineering sector is bringing new perspectives to the bone regeneration [as it can be seen from the note reported in the following work: Waese E Y L, Kandel R R, Stanford W L, *Skeletal Radiology* 37(7), pp. 601-608, 2008]. In this field, a fundamental role is played by the mechanical properties of the materials used for making the scaffolds, which are the most usable devices [as reported in several monographic works, among which the following can be mentioned: Stevens M M, *Materials Today* 11(5), pp. 18-25, 2008. Barrere F et al., Materials Science & Engineering R-Reports, 59(1-6), pp. 38-71, 2008]. For sake of completeness, it is to be reminded that in the bone, tendon and cartilage regeneration field, several investigations exist, which provide the use of highly-porous scaffolds imbibed with hydrogel-based matrices, containing, in turn, the cells [See, to this end, for example, the wide bibliography cited in the U.S. Pat. No. 6,171,610].

Generally, briefly, the scientific literature substantially identifies four possible paths to regenerate tissues:

a) stimulating independent endogenous regeneration mechanisms—an approach founded on bases, which are not solid yet, and with procedures, not well-identified yet, as a whole not really promising at the moment;

b) transplanting isolated cells directly in the injured site—an empirical approach, based on a good functional principle, but that brings along a number of drawbacks and problems, such as the high cell loss and the resulting low integration with the adjacent tissue;

c) transplanting tissue generated in vitro (also called graft)—an empirical approach based on a good tissue principle, but with remarkable complexities, since the graft needs to integrate with the adjacent tissues, at its best, be capable of withstanding the possible mechanical stress it undergoes once in vivo and, possibly, have a suitable bioabsorbability with the target tissue;

d) using advanced micro- and nano-structured materials, which are capable of hosting specific cell populations providing a compatible and favourable environment, which, subsequently, can be used as a carrier for the implant—futuristic approach, based on rational principles, but that still needs a full comprehension of the phenomena involved.

Whatever approach is followed, the procedures presently available often allow only a partial, if any, reconstruction to be achieved. This limited success depends on several reasons, and, mainly, they have to be found in the cellular aspects and in the lack of a suitable physical support for the thus transplanted, or injected, cells, during the time between the implant and the integration with the adjacent tissues. Moreover, when a suitable nutrient-permeable support is missing, cells cannot obtain the necessary nutrients to survive and eliminate the catabolytes.

The above reasons are leading the research to be addressed towards the development of support matrixes, which allow to carry cells, allowing and/or increasing the same to survive and integrate with the target tissue, in order to give rise to a new functional tissue, histologically integrated with the adjacent structures.

In view of the foregoing, besides the cells, an essential element of tissue engineering is therefore represented by the support and carrier materials used, among these, hydrogels play a key role, since they are useful as support and carrier systems for cells and cell populations.

However, even though the literature about this topic is quite comprehensive, the specifically suitable hydrogels for hosting cells, particularly of the central nervous system, are a minority. To this end, see what is reported in the following literature: Huang et al. *Journal of Neurosurgery* (2008) vol. 108 pp. 343-347; Crompton et al. *Biomaterials* (2007) vol. 28 pp. 441-449; Frampton et al. *Journal of Neural Engineering* (2007) vol. 4 pp. 399-409; Hind et al. *Journal of Biomaterial Science Polymer Edition* (2007) vol. 18 pp. 1223-1244; Mahoney et al. *Biomaterials* (2006) vol. 27 pp. 2265-2274; Prang et al. *Biomaterials* (2006) vol. 27 pp. 3560-3569; Luo et al. *Nature Materials* (2004) vol. 3 249-253; Vacanti et al. *Transplantation Proceedings* (2001) vol. 33 pp. 592-598; Woerly, EP0929323). This is mainly due to the difficulties in making hydrogels, which allow the cells, in particular the central nervous system cells, to survive and grow therein, by providing them both support and a suitable viable space.

In some cases, the mechanical functionality requirements make the use of scaffolds indispensable, but the target tissues very often require to be inundated by a cell flow, which is stable and allows the reintegration thereof, and this can be achieved by using proper hydrogels. As already stated, in some cases, mixed solutions may be used, wherein the solid scaffolds are imbibed with hydrogels containing or supporting the cells.

Hydrogels are tri-dimensional polymeric structures, capable of swelling by retaining water, or other liquids, therein. The polymeric chains are linked to each other through intermolecular bonds, which can have a different origin. Hydrogels can be produced in a number of ways, one of which consists in reacting one or more monomers or due to the association of hydrogen bridges or strong van der Waals interactions among polymeric chains. According to the components used, the hydrogels can be biodegradable or biostable, biocompatible or cytotoxic. A lot of biocompatible, biodegradable or not, hydrogels are gaining interest from the technical-scientific world, due to their inherent characteristics, which make them particularly suitable and ideal for many applications in the bio-medical field.

From a strictly chemical point of view, hydrogels can be classified in several ways, according to their preparation method, the distributed ion charge or their physical structure. In relation to the preparation, hydrogels can be classified as homopolymeric, co-polymeric, multi-polymeric or interpenetrating polymeric hydrogels. The firsts are made by polymeric networks, bound to each other by a monomer unit, which has to be hydrophilic. The seconds are made of two co-monomers, at least one of which is to be hydrophilic. The multi-polymeric ones are obtained starting from three or four co-monomers interacting with each other, at least one being hydrophilic. Finally, the interpenetrating polymeric ones are obtained through swelling a first network, around which, subsequently, a tri-dimensional structure is formed.

Therefore the chemical and physical properties of hydrogels make them particularly suitable for being used in the biomedical and pharmaceutical fields. In particular, their biocompatibility is the first fundamental requirement for such applications.

Their hydrophilicity can guarantee optimal features in terms of gas- and other substances-permeability, allowing also the controlled release of active substances and supporting the presence of cell populations inside or on their surface. One of the first applications developed, still widely spread today, is linked to manufacturing contact lenses where hydrogels are used due to their good mechanical stability, the favourable refractive index and their high oxygen permeability. Other applications, such as those described in the present application, include using hydrogels as bio-adhesive artificial materials, artificial membranes, articular cartilages, artificial skin, materials for the maxillo-facial and vocal cord reconstruction.

It is to be highlighted that hydrogels find a wide use also as in vitro cell growth support, in pharmacological screening applications, drug-development assay, pharmacological efficacy or toxicity or other electro-physiological or bio-mechanical features. Some of these assays are carried out through devices, also known as bioreactors and "biochips".

For example, such supports are usually configured as thin films, on which neurons are laid and grown. Therefore, they are bi-dimensional structures on which neurons are laid on one of the surfaces and not placed therein. Among the other hydrogels, devised and developed for these uses, the most used are Matrigel™ (Beckton Dickinson, USA) and fibrin or collagen gel (Viscofan S/A, Spain).

It is to be reminded that the recent advances in electronics have made available for neuroscientists several technological solutions, which allow the communication between specific electronic devices and living neuronal cells. Measuring devices are, in fact, available on the market, specifically made for monitoring the cell activity of individual neurons or populations of neurons, during several kinds of testing, ranging from monitoring the signal conductivity to pharmacological efficacy. In such electronic systems, the contact between neurons and an electronic substrate is often mediated by a thin (a few microns) film of polymeric hydrogel, suitably designed and made in order to allow the passage of both electrical and chemical signals.

The technical-scientific literature available, regarding the materials, including hydrogels, and their use in the regenerative field, is very wide, in the nervous regeneration field, it is to be considered the recent review carried out by Little et al. *Chemical Reviews* (2008) vol. 108 pp. 1787-1796, and in this wide survey, hydrogels are, per se, known and they are often described as means for controlled drug-delivery and supports for tissue engineering [as it can be inferred from the monographic reviews cited below as a way of example: J. D. Kretlow et al., *Advanced Drug Delivery Reviews* 59 pp. 263-273, 2007. L. Yu et al., Tutorial Review on Chemical Society Reviews, 2008].

The preparation of several anionic gels for the controlled drug delivery was described in 1986 by Hsu et al. in *Pharmaceutical Research* (1996) vol. 13 pp. 1865-1870. In particular, the preparation of a two-component hydrophilic gel made of an agarose and carbomer formulation. This particular gel is prepared by mixing an aqueous carbomer dispersion with a pre-heated agarose dispersion at a certain temperature.

The European patent EP0929323 describes a biostable (and therefore biodegradable) polymeric hydrogel for therapeutic use, consisting in a copolymer of (a) an N-substituted methacrylamide or acrylamide (b) a cross-linking agent and (c) co-polymerisable material, which can be used for reconstructing the damaged cerebral or spinal tissue.

The European patent EP1206254 describes a tri-dimensional matrix based on re-absorbable fibers, loaded with specific drugs, wherein cells are grown in vitro, and are subsequently implanted in vivo.

The patent application US2007010831 describes an implant for repairing damaged nerves, comprising an external biocompatible perforated conduit and an inner hydrogel matrix made of agar, agarose, xanthan gum, carbopol, alginate salts, polyvinylpyrrolidone, polyethylene glycole, chitosane, cellulose, acrylics and polyglycolic polymers and other natural or synthetic polymers.

U.S. Pat. No. 6,171,610 is also mentioned, where formulations are described, obtained by mixing biocompatible substances, and their extended applications to all the possible cell populations and in particular to the central nervous system tissue.

DESCRIPTION OF THE INVENTION

Aim of the present invention is to provide a polymeric matrix based on biodegradable compounds, which can be used in its swell status as a housing and conveying device for several kinds of cells for regenerating and/or reconstructing and/or replacing several damaged, dead or no longer functional living tissues, such as central nervous system cells, for example neuronal cells, for regenerating soft tissues within the central nervous system itself.

Said object is achieved through a double polymeric interpenetrating matrix hydrogel comprising an acrylic acid-based or carbomeric polymer, a natural polymer selected among agarose, chitosan, dextran, a polysaccharide or a glycosaminoglycane, a cross-linking agent selected among glycerol, propylene glycol, ethylene glycol, triethylamine or a mixture thereof and, eventually, an elasticizing agent selected among alginic acid and salts thereof, any kind of collagen or derivatives thereof, fibrin, fibrinogen and hyaluronic acid or a derivative thereof, such as, for example, gelatine, laminine, polyethyleneglycol (PEG) or a mixture of said agents, said hydrogel containing cells placed on its external surface or hosted within the tri-dimensional polymeric matrix, that is within the tri-dimensional lattice of the matrix itself.

The polymeric matrix may comprise, preferably, (% by weight) from 0.01% to 5% of acrylic acid-based or carbomeric polymer, from 0.01% to 5% of natural polymer, from 0.1% to 40% of cross-linking agent, and, eventually, from 0.01% to 5% of elasticizing agent.

According to a preferred aspect, the hydrogel comprises carbopol, as acrylic polymer, agarose, as natural polymer, and a mixture of glycerol, propylene glycol and triethylamine, as cross-linking agent and in another particularly preferred aspect, the hydrogel further comprises gelatine or PEG, as elasticizing agent.

Further, the hydrogel can comprise nutrients and/or growth factors for cells, in particular for neuronal cells.

Such nutrients and/or growth factors for cells may be selected among: saline buffer, B27 (GIBCO®, Invitrogen, USA), Insulin-Transferrin-Selenium-G Supplement, D-(+) Glucose, L-Glutamine, Penicillin-Streptomycin, Sodium pyruvate, MEM (Minimum Essential Medium) Vitamins 100×, MEM Aminoacids 50×, MEM Non-Aminoacids 100×, NEAA (Non-essential Amino Acids), HEPES (4-2-hydroxyethil-1-piperazinil-ethanesulfonic acid) Buffer, bicarbonate, carnitin (Alcar), D-vitamin, L-arginine.

According to a particularly preferred aspect, the hydrogel can further comprise one or more drugs and/or factors and/or active substances, capable of modulating the action of the cells and/or keeping them viable and/or stimulating their metabolism and/or stimulating their growth and development and/or stimulating their differentiation and/or stimulating the interaction and mutual interconnectivity.

Another aspect of the present invention relates to the use of said hydrogel for preparing a cell implant for regenerating or reconstructing or replacing damaged or dead or removed or non-functioning, even partially, tissues, such as, for example, the nervous tissue of the central nervous system, such as the neuronal tissue and the spinal tissue. Indeed, through the present invention, the tissue in the zone of said implant can be improved and cured by supplying cells and controlling their proliferation, infiltration and integration with the tissue surrounding the implant zone.

Another aim the present invention is to provide a means for tissue regeneration in different body zones, in particular of the central nervous system and of the spinal marrow, by using a biodegradable polymeric matrix, particularly beneficial, both clinically and cost-effectively, for patients suffering from degenerative pathologies, as a result of traumas, resections or other pathologies, for neurological patients, such as the spinalized patients, or those, who suffered from ictus or surgical operations due to cerebral or spinal tumours, or, further, those suffering from neurodegenerative pathologies such as for example Alzheimer o Parkinson.

Another object of the present invention is to provide a means for regenerating several living tissues, such as, for example, those of the central nervous system and the spinal marrow, with such characteristics that it can be easily positioned in the target zone by means of traditional surgical or mini-invasive techniques and that it can be easily adapted to the dimensions of the implant site.

Another aspect of the present invention is a method to prepare said hydrogel, which comprises the preparation of an aqueous dispersion comprising (% by weight) from 0.01% to 5% of acrylic acid-based or carbomeric polymer, from 0.01% to 5% of natural polymer, from 0.1% to 40% of cross-linking agent, and, optionally, from 0.01% to 5% of elasticizing agent, at a temperature of 20-90° C. and for a time ranging from 10 seconds to 240 minutes, as a function of the desired cross-linking grade and of the polymers used, and the possible subsequent cooling down to a temperature ranging from 37° C. and room temperature. To said polymer mixture a base can be added, capable of neutralizing the acid, which develops during the reaction, preferably selected among triethylamine and ammonia.

Further, to the polymer mixture suitable salts or saline solutions or buffer solutions, directed to control the pH may be optionally added.

According to a preferred aspect, the added buffer solution is PBS (Phosphate buffer saline), according to a further particularly preferred aspect, to the polymer mixture, both the base triethylamine and the buffer solution PBS and NaOH are added.

The weight ratios between the several components can be varied in the above defined ranges, thereby enabling to modulate the dimensions of the polymeric lattice mesh, according to the cell type to be carried in order to make the matrix more suitable to each specific population. Preferably the polymers and all the reagents used meet the purity and sterility standards required for medical, biological, biomedical and pharmaceutical applications.

It is another object of the present invention to provide a new polymer mixture with the proper chemical-physical characteristics, so that living cells can be mixed therein, guaranteeing the cells survival and proliferation.

Therefore, it is another aspect of the present invention a method for making a bi-dimensional or tri-dimensional bio-hybrid device, which can be used for housing and conveying cells for living tissue regeneration within the human body, in particular central nervous system cells, such as, for example, neuronal cells, for the regeneration of soft tissues within the central nervous system. A further basic characteristic is that such device degrades with a kinetics predetermined and compatible with the integration between conveyed cells and target tissue.

Another aspect of the present invention relates to a method for the preparation of a device based on said hydrogel containing cells, in general, and in particular cells of the central nervous system, more particularly neuronal cells. Said cells can be drawn from a fresh tissue or kept in a culture, away from the support (for example a Petri dish or other), eventually washed and subsequently added to the polymer mixture, cross-linking agent and optionally elasticizing agent during the gelling process, preferably during the cooling step. In order to keep the highest number of cells trapped in the hydrogel matrix in a viable status and in growing conditions, it is preferable to add a suitable culture medium to the aqueous dispersion of polymers, before gelling. Alternatively, the cells trapped in the polymeric matrix can be supplied with nutrients and factors necessary for their growth, contacting or immersing the hydrogel in a proper culture medium. Moreover, during the gel preparation, one or more drugs and/or active substances and/or specific factors and/or other substances can be added, which are capable of modulating the specific action of the cells, for example the central nervous system cells, particularly the neuronal cells, also according to the target tissue to be regenerated, and that are gradually released from the polymeric matrix once the implant has been introduced in the target tissue.

Such drugs and/or active substances and/or specific factors and/or other substances, added during the preparation of hydrogel, are capable of keeping the cells viable and/or stimulating their metabolism and/or stimulating their growth and development and/or stimulating their differentiation and stimulating the interaction and mutual interconnectivity.

Moreover, the aqueous polymeric mixture can be replaced with a culture medium, suitable for keeping the cells in viable and growing conditions.

According to an embodiment, during the preparation of the hydrogel, said aqueous mixture or said suitable culture medium can contain, additionally, the above-described nutrients and/or growth factors.

Another aspect of the present invention is the use of a hydrogel, having a high capacity to swell, to embed a mixture, mainly based on water, and a culture medium, eventually added with factors and/or other active substances, said mixture being suitable to provide the hosting cells with the necessary nutrients, so that they can survive and proliferate within the hydrogel.

Another aspect of the present invention is the use of a suitable culture medium, directed towards an improvement of the viable conditions of cells, once encapsulated in the gel. Such medium can be used directly for making the gel with or without adding a buffer saline solution.

Several kinds of cells can be used for preparing said bio-hybrid device according to the invention, such adult, embryonic, stem, wild-type, engineered, non-engineered, primary or immortalized (cell-line) cells.

According to a preferred aspect, the cells used are central nervous system cells, in particular neuronal cells.

In an embodiment of the present invention, the hydrogel has suitable chemical-physical characteristics to be produced in the form of a thin film by one of the methods known in the state of the art such as, by way of example and not comprehensive, spindle spin-coating with subsequent cooling, spindle dip-coating with subsequent cooling or sol-gel. The hydrogel thus obtained has a thickness in the order of the dimensions of the cells to be hosted (from a few micrometers to a few tenths of millimeter).

Another aspect of the present invention relates to the use of said hydrogel, produced in the form of a thin film as a support for the cellular growth in vitro in pharmacological screening, assay for the drug-development, pharmacological efficacy and toxicity applications. Such a support is made as a thin film on or in which individual cells or cell populations are laid and grown, such as, for example, individual neural cells or neural cells populations, in particular neuronal cells, also different from each other. Such a support is also made as a linking substrate between cells, such as central nervous system cells, in particular neuronal cells, and measuring devices, specifically realised to monitor the cellular activity of individual cells or cell populations during different kinds of tests, from the monitoring signal conductivity (for example for the excitable cells, such as heart or nervous cells), to the pharmacological efficacy. Such a thin polymer hydrogel film should be specifically designed and realized in order to allow electrical and chemical signals to pass. The high porosity of the hydrogel structure, together with the presence of electrolytes in the aqueous solution, allows high values of electrical conductivity (comparable to those measured in the solution itself) and ion diffusion to be obtained.

In a preferred aspect, the hydrogel can be used as an interface between cells and electronic devices.

Such a hydrogel can be also realized in the form of a thin film assembly, arranged on multiple overlapping layers and suitable for supporting and hosting different cell populations, in order to obtain a poly-functional advanced structure (Multi Layer Systems).

In a preferred embodiment of the invention, the hydrogel is obtained from a mixture containing carbopol, agarose, glycerol, and propylene glycol, in presence of triethylamine, dispersed in a proper aqueous medium, to which a nutrient mixture is added, such as, for example, glucose, essential amino-acids, proteins, oligo-elements, mineral salts, vitamins and bactericidal antibiotics. Such a hydrogel containing the cells, can be positioned, conveniently, within wells suitable for the cell culture. The encapsulated cells in the tridimensional matrix remain viable and keep on growing and aggregating, as it could be seen during the experiments, when the cell morphology, viability and proliferation within the above described hydrogel were assessed.

In another preferred embodiment of the invention, the hydrogel is obtained from a mixture containing carbopol, agarose, glycerol and propylene glycol, in presence of triethylamine, dispersed in an proper aqueous medium. Such hydrogel is within a hollow circular support and rotated to such a speed that a thin and regular film may be obtained once cooled. Subsequently, on this hydrogel film, once removed from the support and positioned in a micro-electronic device, a liquid dispersion, containing cells, for example central nervous system cells, in particular neuronal cells, is laid. Likewise, within the mixture, cells can be directly positioned and therefore a thin film containing the same cells can be produced by means of the described method.

A further aspect of the invention relates to the use of a hydrogel as described above, in any embodiment thereof, for preparing a cell implant for, integrally or partially, regenerating or reconstructing damaged or ill or removed tissues, in particular muscle, myocardium, connective, bone, tendon or ligamentous, hepatic, renal, corneal, dermis or epidermis, articular cartilagenous tissue.

According to a further aspect, such a hydrogel, as described above, in any embodiment thereof, can be used for preparing an implant of central nervous system cells as neuronal cells for, integrally or partially, regenerating or reconstructing neuronal tissue, in particular central nervous system tissue, nervous tissue, such as neuronal tissue, damaged as a result of Parkinson's disease or spinal marrow damages or oncologic pathologies or Alzheimer's disease, nervous tissue, such as neuronal tissue, removed or ablated, following an surgical operation.

In the state of the art, the addition of cross-linking compounds, capable of modifying the mechanical properties of polymers at the hydrogel base, the addition of buffering substances, capable of neutralizing acidity which develops during the gel formation process and during the subsequent decay due to the cross-linking reactions, the addition of elasticizing compounds are not mentioned. Moreover, the possibility to apply such a gel to the living tissue engineering is not mentioned, and other specific applications, other than drug release, are not provided. Besides, the addition of culture media and/or factors or active substances, suitable for providing cells with the necessary nutrients and modulate their action and activity are not referenced.

In case of mixtures of agarose and carbomer, for example, the use of cross-linking agents and acidity buffers results not only to be fundamental for controlling the gelling, but also for obtaining a suitable matrix for hosting the specific selected cells and for conveying them, keeping them viable and, thereby, guaranteeing their survival and therapeutical efficacy once implanted in situ. It is to be pointed out that the more efficient the polymeric matrix, obtained in a gel form, is, when enabling the cell support, viability and proliferation therein, the more the gel structure matrix conformation fits that of the extracellular matrix, expected by the cells.

Briefly, the prior analysis shows that hydrogels, mainly based on carbomer and agarose, are not described, whose mechanical properties, and thereby also their biodegradability, are modulated by the addition of cross-linking compounds, such as propylene glycol, glycerol and triethylamine, containing cell nutrients, active substances and/or drugs and employed as cell support and carrier means, for example for central nervous system cells, such as neuronal cells, for tissue regeneration and reconstruction applications.

EXAMPLES

The following examples illustrate the invention in more detail.

Example 1

Preparation of Hydrogel with Two Different Possible Concentrations and with Myoblast Cells (Line C2C12) to be Inserted Therein The procedure below leads to form a hydrogel with a portion of 0.5% carbomer and 0.5% or 0.25% agarose, and with myoblasts therein.

Required reagents for preparing 100 mL of gel with neuronal cells:

Carbomer 974 P (CAS151687-96-6, Fagron, Bufa, Netherlands): 0.5 g
Agarose (CAS 9012-36-6, Invitrogen Corp., Carlsbad, USA): (0.5 g or 0.25 g)
Propylene Glycol (CAS 504-63-2, Sigma-Aldrich, Germany): 30 mL
Glycerol (CAS 56-81-5, Merck Chemicals, Germany): 1 mL
Triethylamine (CAS121-44-8, high purity preparation, Sigma-Aldrich, Germany): 0.5 mL
PBS: sufficient quantity (qs)
Cells: C2C12 (mioblasts)
Culture medium: DMEM (Dulbecco's Modified Eagle's Medium, Sigma-Aldrich Germany).

Operating procedure for preparing the cells. Such a procedure starts with the following cell thawing operations from the cryopreservant solution, to be carried out entirely under a class II sterile hood:

1. draw the required portions of cryopreserved cells in their cryovial;
2. draw 10 mL of culture medium and transfer it in a 50 mL tube, keeping it at T=37° C.;
3. draw 1 mL of medium from the tube and transfer it to the cryovial containing the cryopreserved cells and gently stir with the pipette in order to dissolve the cryopreservant contacting the cells, to obtain their full thawing;
4. upon the full thawing, transfer the whole solution with the cell suspension from the cryiovial to the tube containing the medium and carry on with suspending again the cells in the tube with the culture medium;

5. transfer the tube with the cells in the centrifuge and centrifuge for 5 minutes at 2000 rpm;

6. remove the culture medium from the tube, leaving the cells on the bottom, then add 1 mL of fresh culture medium and suspend again the cells;

7. carry out the cell count (for example in a Neubauer chamber) and then draw a suspension volume, which contains the intended number of cells to be sowed in the flask and transfer it therein; in such a case for a concentration of 100,000 units/mL;

8. leave the flask inside a suitable cell incubator for the time required for the cells to reach a sufficient confluence.

Operating procedure for preparing the gel, under a class II sterile hood:

1. in a pirex Becker weigh carbomer and add the respective quantity of PBS, under stirring (1400 rpm, with hook) for 30 minutes at room temperature (T=25° C.);

2. add glycerol and propylene glycol, keeping under stirring at the same speed for further 20 minutes, still at room temperature;

3. leave the suspension without stirring for 60 minutes at room temperature;

4. in order to neutralize the solution pH (if necessary) add a 98% triethylamine in water q.s., slowly mixing for 10 minutes under slow stirring (250 rpm, with hook);

5. weigh and add powdered agarose according to the previously predetermined concentration and keep under stirring (250 rpm, with hook) for 5 minutes at room temperature;

6. heat the solution with an electromagnetic radiation (500 W) for about 2 minutes until a temperature of about 80° C. is reached;

7. after the solution has been drawn, during the cooling step, at about 40° C., add the previously prepared solution containing the cells, in a volume ratio 1:1, keeping the new solution thus obtained slightly rotating;

8. draw, from the final gel and cell solution, the required quantity to fill the cell culture wells used, which will have to be filled at 50% of their total volume by the final gel and cell solution (applicable standard wells are the 48-well plates "multiwell"), fill the remaining volume with the culture medium suitable for the cell type in use (supernatant medium);

9. for maintaining the gel with cells inside, it is necessary to place the samples in an appropriate cell culture incubator and replace the supernatant medium every 24 hours with a fresh one.

Operating procedure for cell activity assays, aimed to assess the cell morphology, viability and proliferation of the encapsulated cells within a hydrogel, made as described in the previous procedures.

In order to assess the cell viability, carry out, daily, the assays MTT (3-(4,5-dimethylthiazol-2-yl)-2,5-diphenyltetrazolium bromide, Sigma-Aldrich, Germany) and Alamar Blue™ (AbD Serotec, Great Britain) on the prepared samples as for the above described procedures. On the other side, the cell morphology can be visibly compared by a scanning optical and/or electron microscope.

A confirmation of the cell viability and proliferation status can be achieved by carrying out the above assays on the cells, once drawn from the gel. Such an operation is seen as destructive for the gel, but non significantly for the cells, and taking care for designing a sufficiently wide experimental set, it can also be carried out in different times. Such drawing can be achieved through the following operating procedure, to be carried out under a class II sterile hood:

1. recover the supernatant from the wells containing the samples and transfer it into a 50 ml tube and bring it to a 30 ml volume by adding a PBS and SSPE (Saline Sodium Phosphate-EDTA, Ethylene Diamine Triacetic Acid) 1× (Sigma-Aldrich, Germany) solution, q.s., and carry out a first centrifuge at 2000 rpm for 5 minutes;

2. at the end of the centrifuge, eliminate the supernatant and suspend again with 30 mL of the previously described solution PBS/SSPE 1×, to which 0.5 mL trypsin-EDTA 1× (Sigma-Aldrich, Germany; EDTA=Ethylene Diamine Triacetic Acid, ethylene-diamine-triacetic acid) solution is to be added;

3. in the wells, where the samples are placed, add 0.5 ml of the previously described solution PBS/SSPE 1×, to which 0.5 mL of the previously described trypsin-EDTA 1× solution is to be added and place in a suitable incubator for at least 5 minutes;

4. after the incubation, recover the whole content from the wells and transfer it into the same, previously used, 50 mL tube, then carry out a second centrifuge at 2000 rpm for 5 minutes;

5. at the end of the centrifuge, recover the supernatant in a second 50 mL tube and suspend again what left in the first tube with 20 mL of the previously described PBS/SSPE 1× solution, to which 1 mL of the previously described trypsin-EDTA 1× solution are to be added.

6. carry out a third centrifuge of both 50 mL tubes, at 2000 rpm for 5 minutes;

7. at the end of the centrifuge, eliminate the supernatant from both tubes, suspend what left in both tubes with 20 mL of the previously described PBS/SSPE 1× solution;

8. join the contents of the two tubes in one single tube and start a fourth centrifuge at 2000 rpm for 5 minutes;

9. at the end of the centrifuge, eliminate the supernatant and suspend in a suitable medium;

10. remove the suspension from the tube and transfer it in the proper flask for the storage in a proper incubator.

Example 2

Preparing the Hydrogel with Two Possible Different Concentrations and with Cells of the Line P19, Phenotype CL6 (that is Embryonic Stem-derived Contractile Cardyomiocytes) to be Inserted Therein and a Specific Culture Medium for this Population The same procedures are applied as described referring to the example no. 1, where Alpha-MEM (Invitrogen, USA) is used instead of the culture medium DMEM.

Example 3

Preparing the Hydrogel with Two Possible Different Concentrations and Two Different Kinds of Nervous Tissue Cells to be Alternatively Inserted Therein The procedure below leads to form a hydrogel with a portion of 0.5% carbomer and 0.5% or 0.25% or 0.125% agarose and with neural cells therein.

Required reagents for preparing 100 mL of gel with neuronal cells:

Carbomer 974 P (CAS151687-96-6, Fagron, Bufa, Netherlands): 0.5 g

Agarose (CAS 9012-36-6, Invitrogen Corp., Carlsbad, USA): (0.5 g or 0.25 g or 0.125 g)

Propilene Glycol (CAS 504-63-2, Sigma-Aldrich, Germany): 30 mL

Glycerol (CAS 56-81-5, Merck Chemicals, Germany): 1 mL

Triethylamine (CAS121-44-8, high purity preparation, Sigma-Aldrich, Germany): 0.5 mL PBS: qs Cells: U87 (neuroglia) or N9 (microglia)

Culture medium: DMEM (Dulbecco's Modified Eagle's Medium, Invitrogen Corp., Carlsbad, USA) for U87, or IMEM (Iscove's Mi-nimal Essential Medium, Sigma-Aldrich, Germany) for N9.

The operating procedure for preparing the cells is carried out as described in the above example no. 1, however, in this case, the concentration as in point 7 of the procedure is 40,000 units/mL. The gel is prepared, under a class II sterile hood, according to the operating procedure described in the previous example no. 1.

The cell activity of U87 or N9 cells is measured following the operating procedure described in the previous example no. 1.

Once the cells are extracted from the gel, further assays and measurements of the activity may be performed, such as, for example imaging of the calcium ion. Such an extraction can be achieved by the operating procedure, to be carried out under a class II sterile hood, described in the previous example no. 1.

Example 4

Preparing the Hydrogel with Two Possible Different Concentrations and with Cells of the Line N9 (Microglia) to be Inserted Therein and a Specific Culture Medium for this Population The same procedures are applied as described in the previous example no. 1, wherein, instead of the culture medium DMEM, the following medium is used, obtained as a specifically realized solution for promoting these cells within the gel; reagents' quantities suitable for 20 mL solution:

| | |
|---|---|
| PBS (Sigma, Germany) | 18,790 mL |
| B27 (GIBCO ®, Invitrogen, USA) | 400 µL |
| Insulin-Transferrin-Selenium-G Supplement, 100X (GIBCO ®, Invitrogen, USA) [dilution 1:100] | 10 µL |
| D-(+)Glucose @ 45% (Sigma G8769, Germany) | 80 µL |
| L-Glutamine (Sigma G7513, Germany) | 200 µL |
| Penicillin-Streptomycin (Sigma P0781, Germany) | 60 µL |
| Sodium pyruvate (Sigma S8636, Germany) | 200 µL |
| MEM Vitamins 100X (Sigma M6895, Germany) | 20 µL |
| MEM Aminoacids 50X (Sigma M5550, Germany) | 20 µL |
| MEM Non-Aminoacids 100X NEAA (Sigma M7145, Germany) | 20 µL |
| HEPES Buffer (Sigma H0887, Germany) | 200 µL |

Reagents are added in sodium bicarbonate and the solution is diluted, 1:100 and drawn in portions as large as necessary.

Example 5

Preparing the Hydrogel with Two Possible Different Concentrations and with Two Different Kinds of Cells of the Nervous Tissue to be Alternatively Inserted Therein and a Specific Culture Medium for the Cell Populations in the Nervous System The same procedures are applied as described in the previous example no. 3, where, instead of the culture media DMEM and IMEM, for U87 and N9, respectively, the following medium is used, obtained as a specifically realized solution for promoting the neuronal cells within the gel; reagents' quantities suitable for 20 mL solution:

| | |
|---|---|
| Nutrient Mixture F-12 Ham (Sigma N4888, Germany) | 18,790 mL |
| B27 (GIBCO ®, Invitrogen, USA) | 400 µL |
| Insulin-Transferrin-Selenium-G Supplement, 100X (GIBCO ®, Invitrogen, USA) [dilution 1:100] | 10 µL |
| D-(+)Glucose @ 45% (Sigma G8769, Germany) | 80 µL |
| L-Glutamine (Sigma G7513, Germany) | 200 µL |
| Penicillin-Streptomycin (Sigma P0781, Germany) | 60 µL |
| Sodium pyruvate (Sigma S8636, Germany) | 200 µL |
| MEM Vitamins 100X (Sigma M6895, Germany) | 20 µL |
| MEM Aminoacids 50X (Sigma M5550, Germany) | 20 µL |
| MEM Non-Aminoacids 100X NEAA (Sigma M7145, Germany) | 20 µL |
| HEPES Buffer (Sigma H0887, Germany) | 200 µL |

Example 6

Preparation of the Hydrogel with Two Possible Different Concentrations, with an Elasticizing Agent and with L929 Cells (Fibroblasts) to be Inserted Therein The same procedures are applied as described in the previous example no. 1, wherein, the PBS used for preparing the gel is added with 0.5% by weight of gelatine (Sigma-Aldrich, Germany).

Example 7

Preparing the Hydrogel with Two Possible Different Concentrations, with an Elasticizing Agent and with Two Different Kinds of Cells of the Nervous Tissue to be Alternatively Inserted Therein The same procedures are applied as described in the previous example no. 3, wherein, the PBS used for preparing the gel is added with 0.5% by weight of alginic acid (Sigma-Aldrich, Germany).

Example 8

Preparing a Hydrogel Thin Film and with Two Different Kinds of Cells of the Nervous Tissue to be Grown Thereon The same procedures are applied as described in the previous example no. 3, wherein, a proper quantity of gelatinous solution, once heated and when it is still in a melted state, is laid on a specific hollow and circular support. Such a support is rotated at a proper speed with the desired final target thickness, while the solution itself is left to cool at room temperature. Once cooled, the hydrogel film is removed from the support and placed in a cell culture well, on which a liquid dispersion containing neuronal cells is laid.

Example 9

Preparing the Hydrogel with Two Possible Different Concentrations, with the Addition of Specific Factors for the Cell Populations of the Central Nervous System or the Myocardium Cells The same procedures are applied as described in the previous example no. 1, wherein, the culture medium is the one described in example no. 4 and is added with carnitine (alcar) in a concentration ranging from 30 to 100 millimolars, to best promote the central nervous system-derivated cells, or, alternatively, said culture medium is added with D vitamin in one of its variants (such as, by means of example and not limitative, cholecalciferol), at a concentration of about 0.0004 g/ml, in order to best promote the cardiomyocyte cell populations.

What is claimed is:

1. A double interpenetrating polymeric matrix hydrogel comprising:
   an acrylic, acid-based polymer including carbopol;
   a natural polymer including agarose; and
   a cross-linking agent including a mixture of glycerol, propylene glycol, and triethylamine.

2. The double interpenetrating polymeric matrix hydrogel of claim 1, further comprising an elasticizing agent that includes at least one of alginic acid and salts thereof, collagen and derivatives thereof, fibrin, fibrinogen, hyaluronic acid and derivatives thereof, laminine, gelatine, polyethylene glycol (PEG), and a mixture thereof.

3. The double interpenetrating polymeric matrix hydrogel of claim 2, wherein said acrylic acid-based polymer is in a range of between from 0.01% to 5% by weight, said natural polymer is in a range of between from 0.01% to 5% by weight, said cross-linking agent is in a range of between from 0.1% to 40% by weight, and said elasticizing agent is in a range of between from 0.01% to 5% by weight.

4. The double interpenetrating polymeric matrix hydrogel of claim 2, wherein said elasticizing agent comprises gelatine.

5. The double interpenetrating polymeric matrix hydrogel of claim 1, further comprising a plurality of cells.

6. The double interpenetrating polymeric matrix hydrogel of claim 5, wherein said plurality of cells comprises at least one of adult, stem, embryonic, wild-type, engineered, non-engineered, primary and immortalized (cell-line) cells.

7. The double interpenetrating polymeric matrix hydrogel of claim 6, wherein said plurality of cells comprises central nervous system cells.

8. The double interpenetrating polymeric matrix hydrogel of claim 7, wherein said central nervous system cells comprises neuronal cells.

9. The double interpenetrating polymeric matrix hydrogel of claim 8, further comprising at least one of nutrients and growth factors for said neuronal cells.

10. The double interpenetrating polymeric matrix hydrogel of claim 9, wherein said at least one of nutrients and growth factors are selected from the group consisting of: saline buffer, B27 (GIBCO®, Invitrogen, USA), Insulin-Transferrin-Selenium-G Supplement, D-(+)Glucose, L-Glutamine, Penicillin-Streptomycin, Sodium pyruvate, MEM Vitamins 100×, MEM Aminoacids 50×, MEM Non-Essential Aminoacids 100×, NEAA, HEPES Buffer, bicarbonate, carnitin (Alcar), D-vitamin and L-arginine.

11. The double interpenetrating polymeric matrix hydrogel of claim 10, further comprising at least one drug, factor and active substances adapted to one of modulate an action of the plurality of cells and/or keeping them viable, stimulate the metabolism of said plurality of cells, stimulate the growth and development of said plurality of cells, stimulate the differentiation of said plurality of cells, and stimulate the interaction and mutual interconnectivity of said plurality of cells.

12. A film comprising:
    a double interpenetrating polymeric matrix hydrogel comprising:
      an acrylic acid-based polymer including carbopol;
      a natural polymer including agarose;
      a cross-linking agent including a mixture of glycerol, propylene glycol and triethylamine.

13. The film of claim 12, wherein the double interpenetrating polymeric matrix hydrogel further comprises a carbomeric polymer.

14. The film of claim 12, wherein the natural polymer further comprises at least one of chitosan, dextran, a polysaccharide, and a glycosaminoglycane.

15. The film of claim 12, wherein the cross-linking agent further comprises ethylene glycol.

16. The film of claim 12, further comprising at least one of an elasticizing agent, a plurality of cells, a nutrient, a growth factor, a drug, a factor, and an active substance.

17. The double interpenetrating polymeric matrix hydrogel of claim 2, wherein the natural polymer further comprises at least one of chitosan, dextran, a polysaccharide, and a glycosaminoglycane.

18. The double interpenetrating polymeric matrix hydrogel of claim 2, wherein the cross-linking agent further comprises ethylene glycol.

19. A double interpenetrating polymeric matrix hydrogel, comprising:
    an acrylic, acid-based polymer including carbopol;
    a natural polymer including agarose;
    a cross-linking agent including a mixture of glycerol, propylene glycol and triethylamine; and
    a carbomeric polymer.

* * * * *